United States Patent
Maloney et al.

(10) Patent No.: US 9,125,826 B2
(45) Date of Patent: Sep. 8, 2015

(54) ORAL CARE COMPOSITIONS

(75) Inventors: Venda Porter Maloney, Piscataway, NJ (US); Suman Chopra, Monroe, NJ (US); Sergio Leite, Monmouth Junction, NJ (US); Long Pan, Cherry Hill, NJ (US); Rahul Patel, Parsippany, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/365,828

(22) PCT Filed: Dec. 21, 2011

(86) PCT No.: PCT/US2011/066496
§ 371 (c)(1),
(2), (4) Date: Jun. 16, 2014

(87) PCT Pub. No.: WO2013/105924
PCT Pub. Date: Jul. 18, 2013

(65) Prior Publication Data
US 2014/0341820 A1    Nov. 20, 2014

(51) Int. Cl.
A61Q 11/00 (2006.01)
A61K 8/02 (2006.01)
A61K 8/28 (2006.01)
A61K 8/41 (2006.01)
A61K 8/37 (2006.01)
A61K 8/44 (2006.01)
A61K 8/49 (2006.01)
A61K 8/34 (2006.01)

(52) U.S. Cl.
CPC . *A61K 8/28* (2013.01); *A61K 8/345* (2013.01); *A61K 8/37* (2013.01); *A61K 8/375* (2013.01); *A61K 8/44* (2013.01); *A61K 8/492* (2013.01); *A61Q 11/00* (2013.01); *A61K 2800/31* (2013.01); *A61K 2800/58* (2013.01)

(58) Field of Classification Search
USPC .......... 424/49, 54, 55; 433/215, 216
See application file for complete search history.

(56) References Cited

U.S. PATENT DOCUMENTS

| | | |
|---|---|---|
| 3,538,230 A | 11/1970 | Pader et al. |
| 3,862,307 A | 1/1975 | Di Giulio |
| 3,937,807 A | 2/1976 | Haefele |
| 3,959,458 A | 5/1976 | Agricola et al. |
| 4,051,234 A | 9/1977 | Gieske et al. |
| 4,340,583 A | 7/1982 | Wason |
| 5,004,597 A | 4/1991 | Majeti et al. |
| 5,188,821 A | 2/1993 | Gaffar et al. |
| 5,192,531 A | 3/1993 | Gaffar et al. |
| 5,244,651 A | 9/1993 | Kayane et al. |
| 5,718,885 A | 2/1998 | Gingold et al. |
| 6,066,314 A | 5/2000 | Tang et al. |
| 7,897,799 B2 | 3/2011 | Pan et al. |
| 2002/0164296 A1 | 11/2002 | Schamper et al. |

FOREIGN PATENT DOCUMENTS

| | | |
|---|---|---|
| EP | 0425018 | 5/1991 |
| EP | 760647 B1 | 12/2001 |
| EP | 1027031 B1 | 8/2005 |
| KR | 2005073925 A | 7/2005 |
| WO | WO 9533441 A1 | 12/1995 |
| WO | WO 2006/068753 | 6/2006 |

OTHER PUBLICATIONS

International Search Report and the Written Opinion issued in International Application No. PCT/US11/66496 mailed Aug. 21, 2013.
Pappas, I., et al., "Thermally Resolved in Situ Dynamic Light Scatterin Studies of Zirconium (IV) Complex Formulation," *Crystal Growth & Design*, 2009 (9):5213-5219. U.S.
Pan, L. et al., "Synthesis and Structural Determination of a Hexanuclear Zirconium Compound Formed in Aqueous Solution," *Inorganic Chemistry*, 2008; 47; 5537-5539. US.
Yao et al., "An investigation of zirconium(IV)—glycine(CP-2) hybrid complex in bovine serum albumin protein matrix under varying conditions," DOI: 10.1039/c1jm13647j. View online at: www.rsc.org/materials. Sep. 19, 2011, US.

*Primary Examiner* — Lezah Roberts
(74) *Attorney, Agent, or Firm* — Anne Louise St. Martin

(57) ABSTRACT

Described herein are compositions comprising zirconium amino acid complexes suspended in a hydrophobic carrier; and methods of making and using the same.

13 Claims, No Drawings

ORAL CARE COMPOSITIONS

CROSS-REFERENCE TO RELATED PATENT APPLICATIONS

The present application is a U.S. national stage entry under 35 U.S.C. §371 of Patent Cooperation Treaty Patent Application No. PCT/US11/66496, filed Dec. 21, 2011, the entirety of which is incorporated herein by reference.

BACKGROUND

The use of zirconium amino acid complexes in oral care formulations has not been reported.

SUMMARY

Some embodiments of the present invention provide a substantially anhydrous oral composition comprising an effective amount of a zirconium amino acid complex suspended in a hydrophobic carrier.

In some embodiments, the present invention provides a method of preventing, reducing or inhibiting dentinal hypersensitivity comprising applying an effective amount of an oral composition comprising a zirconium amino acid complex suspended in a hydrophobic carrier to the oral cavity of a subject in need thereof.

Other embodiments provide methods to reduce the flow rate of fluid through a dentin tubule, comprising applying an effective amount of a zirconium amino acid complex suspended in a hydrophobic carrier to the oral cavity of a subject in need thereof.

DETAILED DESCRIPTION

As used herein, the term "substantially anhydrous" means no water is intentionally added to the composition, but trace amounts of water that may be introduced via other ingredients or processing may exist; but only in amounts that will not prematurely trigger the activity of the active agent(s) in the composition, and/or reduce the stability of the composition.

Some embodiments of the present invention provide a substantially anhydrous oral composition comprising an effective amount of a zirconium amino acid complex suspended in a hydrophobic carrier for preventing, reducing or inhibiting dentinal hypersensitivity.

In some embodiments, the zirconium amino acid complex is selected from a zirconium glycine complex, a zirconium alanine complex, a zirconium arginine complex, and zirconium lysine complex, a zirconium threonine complex, a zirconium leucine complex, a zirconium tryptophan complex, a zirconium phenylalanine complex, a zirconium valine complex, a zirconium methionine complex; and a combination of two or more thereof. In some embodiments, the zirconium amino acid complex is a zirconium glycine complex.

In some embodiments, the hydrophobic carrier is selected from MCT, polyethylene glycol, propylene glycol, silicone fluid, and a combination of two or more thereof. In some embodiments, the hydrophobic carrier is MCT.

In some embodiments, the hydrophobic carrier is a vegetable oil and/or silicone oil. Medium chain triglycerides (MCTs) are preferred as the hydrophobic carrier. MCTs are typically about 6 to about 12 carbons in length. MCTs can be vegetable oils. Caprylic/capric triglyceride is a non-limiting example of an MCT preferred for use in the invention.

In some embodiments, the zirconium amino acid complex is present in the amount of about 0.01 wt. % to about 20 wt. % of the total composition weight. In some embodiments, the zirconium amino acid complex is present at a concentration of from about 0.1 wt. % to about 5 wt. %, of the total composition weight. In some embodiments, the zirconium amino acid complex is present at a concentration of from about 1 wt. % to about 3 wt. %, of the total composition weight. In some embodiments, the zirconium amino acid complex is present at a concentration of about 2 wt. %, of the total composition weight.

For the purposes of the present invention the term "zirconium amino acid complex" is intended to include complexes where the amino acid component has one of more of the nitrogen atoms ionized and is in zwitterion form. Other molecules in zwitterion form could also form a complex with zirconium. One such compound for example is {[3-(Dodecanoylamino)propyl](dimethyl)ammonio}acetate commonly referred to as cocamidopropyl betaine. Thus, some embodiments of the present invention provide compositions comprising a zirconium betaine complex.

In some embodiments, the zirconium amino acid complexes are in the form of particles that are suspended in the hydrophobic carrier. In some embodiments, the hydrophobic carrier comprises from about 5 to about 99% of the total composition weight. In other embodiments, the hydrophobic carrier comprises from about 30 to about 80% of the total composition weight. While in other embodiments, the hydrophobic carrier comprises from about 70 to about 75% of the total composition weight.

The compositions of the present invention can be in any form that when administered will be effective in inhibiting, reducing or preventing (collectively referred to herein as "treating") dentinal hypersensitivity.

The compositions of the present invention can be administered by any suitable means known in the art. In some embodiments, an effective amount of a zirconium amino acid complex suspended in a hydrophobic carrier is administered to the oral cavity of a subject in need thereof.

In some embodiments, the zirconium amino acid complex is formed by a) mixing zirconium (Zr):amino acid:and mineral acid in a molar ratio of 1:about 1 to about 15:about 1.5 to about 3 to form a mixture; b) optionally, filtering the mixture; and c) optionally, drying the mixture.

Some embodiments of the present invention comprise a fluoride ion source. In some embodiments, the fluoride ion source is selected from: stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and a combination of two or more thereof. In some embodiments, the fluoride ion source is present in an amount of about 0.01 wt. % to about 2 wt. % of the total composition weight.

In some embodiments, the composition further comprises an abrasive. In some embodiments, the abrasive is selected from sodium bicarbonate, calcium phosphate (e.g., dicalcium phosphate dihydrate), calcium sulfate, precipitated calcium carbonate, silica (e.g., hydrated silica), iron oxide, alumina (e.g., coated alumina), perlite, zirconium silicate, a plastic particle, e.g., polyethylene, and a combination of two or more thereof. In some embodiments, the abrasive is present in the amount of about 15 wt. % to about 70 wt. % of the total composition weight.

Some embodiments comprise an anionic surfactant selected from:
a. water-soluble salts of higher fatty acid monoglyceride monosulfates (e.g., the sodium salt of the monosulfated monoglyceride of hydrogenated coconut oil fatty acids such as sodium N-methyl N-cocoyl taurate, sodium cocomono-glyceride sulfate), b. higher alkyl sulfates, e.g., sodium lauryl sulfate, c. higher alkyl-ether sulfates, e.g., of formula $CH_3(CH_2)_m CH_2(OCH_2CH_2)_n OSO_3X$, wherein m is 6-16, e.g., 10, n is 1-6, e.g., 2, 3 or 4, and X is Na or K (for example sodium laureth-2 sulfate $(CH_3(CH_2)_{10}CH_2 (OCH_2CH_2)_2 OSO_3Na))$, d. higher alkyl aryl sulfonates (such as sodium dodecyl benzene sulfonate (sodium lauryl benzene sulfonate)), e. higher alkyl sulfoacetates (such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate), f. and mixtures thereof.

By "higher alkyl" is meant, e.g., $C_{6-30}$ alkyl. In particular embodiments, the anionic surfactant is selected from sodium lauryl sulfate and sodium ether lauryl sulfate. In some embodiments, the anionic surfactant is present in an amount of from about 0.3% to about 4.5% by weight.

1.0.1. Any of the preceding compositions further comprising at least one humectant.

1.0.2. Any of the preceding compositions further comprising at least one humectant selected from glycerin, sorbitol, xylitol and combinations thereof.

1.0.3. Any of the preceding compositions further comprising at least one polymer.

1.0.4. Any of the preceding compositions further comprising at least one polymer selected from a polyethylene glycol, a polyvinylmethyl ether maleic acid copolymer, a polysaccharide (e.g., a cellulose derivative, for example carboxymethyl cellulose, or a polysaccharide gum, for example xanthan gum or carrageenan gum), and a combination of two or more thereof.

1.0.5. Any of the preceding compositions comprising gum strips or fragments.

1.0.6. Any of the preceding compositions further comprising flavoring, fragrance and/or coloring.

1.0.7. Any of the preceding compositions further comprising an antibacterial agent selected from a halogenated diphenyl ether (e.g. triclosan), a herbal extract and an essential oil (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, seabuckthorn extract), a bisguanide antiseptics (e.g., chlorhexidine, alexidine or octenidine), a quaternary ammonium compound (e.g., cetylpyridinium chloride (CPC), benzalkonium chloride, tetradecylpyridinium chloride (TPC), N-tetradecyl-4-ethylpyridinium chloride (TDEPC)), a phenolic antiseptic, hexetidine, octenidine, sanguinarine, povidone iodine, delmopinol, salifluor, a metal ion (e.g., zinc salts, for example, zinc citrate, stannous salts, copper salts, iron salts), sanguinarine, propolis and an oxygenating agent (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, a nicin preparation, a chlorite salt; and a combination of two or more thereof.

Some embodiments of the present invention further comprise an antibacterial agent in an amount of about 0.01 to about 5 wt. % of the total composition weight. Some embodiments further comprise triclosan in an amount of 0.01 to 1 wt. % of the total composition weight.

Some embodiments comprise a source of calcium and phosphate selected from (i) calcium-glass complexes, e.g., calcium sodium phosphosilicates, and (ii) calcium-protein complexes, e.g., casein phosphopeptide-amorphous calcium phosphate. Other embodiments comprise a soluble calcium salt, e.g., selected from calcium sulfate, calcium chloride, calcium nitrate, calcium acetate, calcium lactate, and combinations thereof.

Yet further embodiments comprise an orally acceptable potassium salt, e.g., potassium nitrate or potassium chloride, in an amount effective to reduce dentinal sensitivity. Some embodiments comprise from about 0.1% to about 7.5% of an orally acceptable potassium salt, e.g., potassium nitrate and/or potassium chloride.

Some embodiments are in the form of a toothpaste. In some embodiments the toothpaste comprises an arginine salt, e.g., arginine hydrochloride, arginine phosphate or arginine bicarbonate.

In some embodiments, the toothpaste optionally comprises one or more of water, an abrasive, a surfactant, a foaming agent, a vitamin, a polymer, an enzyme, a humectant, a thickener, an antimicrobial agent, a preservative, a flavoring, a colorant and/or a combination of two or more thereof.

Some embodiments comprise a breath freshener, fragrance or flavoring. Other embodiments comprise an anti-calculus agent. In some embodiments, the anti-calculus agent is a polyphosphate, e.g., pyrophosphate, tripolyphosphate, or hexametaphosphate, e.g., in sodium salt form.

Some embodiments provide methods to:

a. reduce or inhibit formation of dental caries, b. reduce or inhibit demineralization and promote remineralization of the teeth, c. reduce or inhibit early enamel lesions, d. reduce or inhibit gingivitis, e. reduce levels of acid producing bacteria, f. to increase relative levels of arginolytic bacteria, g. inhibit microbial biofilm formation in the oral cavity, h. raise and/or maintain plaque pH at levels of at least about pH 5.5 following sugar challenge, i. reduce plaque accumulation, j. whiten teeth, k. improve whole body health, l. reduce erosion of the teeth, m. immunize or protect the teeth against cariogenic bacteria, and/or n. clean the teeth and oral cavity.

In some embodiments, the hydrophobic carrier is capable of suspending the zirconium amino acid complex particles without substantial solubilization of such particles. Examples of suitable hydrophobic carriers are medium-chain triglycerides (MCTs), propylene glycol, polyethylene glycol, silicone fluid, castor oil, and mixtures thereof. Other solvents that are capable of solubilizing the zirconium amino acid complexes optionally may be present in the formulation, provided that it does not adversely affect the efficacy of the composition, e.g. treatment of dentinal hypersensitivity.

MCTs are medium-chain (6 to 12 carbons) fatty acid triesters of glycerol, typically in the form of an oil. These oils can be prepared synthetically by well-known techniques, or can be obtained from natural sources by known techniques of thermal or solvent fractionation of suitable natural oils, such as palm oil or coconut oil, to yield fractions rich in the desired triglycerides. An exemplary low-melting, low molecular weight triglyceride oil is a low molecular weight fraction of coconut or palm oil which is rich in mixed esters of caprylic (octanoic) and capric (decanoic) acids. Such oil is commercially available as Miglyol 812 from SASOL GmbH Germany, CRODAMOL GTCC-PN from Croda Inc. of Parsippany, N.J., or Neobees M-5 oil from PVO International, Inc., of Boonton, N.J. Coconut oil is composed of approximately 66% medium-chain triglycerides. Other rich sources of MCTs include palm kernel oils and camphor tree drupes. The fatty acids found in MCTs are medium-chain fatty acids. The medium-chain fatty acids (and the corresponding number of carbons) found in MCTs are caproic acid (C6), caprylic acid (C8), capric acid (C10) and lauric acid (C12). In another embodiment the approximate ratios of these fatty acids in commercial MCT products derived from coconut oil are 2(C6):55(C8):42(C10):1(C12).

In some embodiments, the compositions may further include one or more fluoride ion sources, e.g., soluble fluoride salts. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as combinations thereof.

In certain embodiments, the oral care composition of the invention may contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A mouthwash, for example, would typically have about 100 to about 250 ppm fluoride. A toothpaste for general consumer use would typically have about 1000 to about 1500 ppm, with pediatric toothpaste having somewhat less. A dentifrice or coating for professional application could have as much as about 5,000 or even about 25,000 ppm fluoride.

Fluoride ion sources may be added to the compositions of the invention at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counter ion in the salt.

In some embodiments, the compositions of the present invention may comprise a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal) or calcium pyrophosphate. Some embodiments may include one or more additional abrasives, for example silica abrasives such as precipitated silicas having a mean particle size of up to about 20 microns, such as Zeodent 115®, marketed by J. M. Huber. Other useful abrasives also include sodium metaphosphate, potassium metaphosphate, aluminum silicate, calcined alumina, bentonite or other siliceous materials, or combinations thereof.

The silica abrasive polishing materials useful herein, as well as the other abrasives, generally have an average particle size ranging between about 0.1 and about 30 microns, about between 5 and about 15 microns. The silica abrasives can be from precipitated silica or silica gels, such as the silica xerogels described in U.S. Pat. No. 3,538,230, to Pader et al. and U.S. Pat. No. 3,862,307, to Digiulio, both incorporated herein by reference. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason, incorporated herein by reference.

In certain embodiments, the silicas are colloidal particles having an average particle size of about 3 microns to about 12 microns, and about 5 to about 10 microns.

In particular embodiments, the abrasive materials comprise a large fraction of very small particles, e.g., having a d50<5 microns, for example, small particle silica (SPS) having a d50 of about 3 to about 4 microns, for example Sorbosil AC43® (Ineos). Such small particles are particularly useful in formulations targeted at reducing hypersensitivity. The small particle component may be present in combination with a second larger particle abrasive. In certain embodiments, for example, the formulation comprises about 3 to about 8% SPS and about 25 to about 45% of a conventional abrasive.

Low oil absorption silica abrasives particularly useful in the practice of the invention are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging about 7 to about 10 microns in diameter, and an oil absorption of less than about 70 cc/100 g of silica is an example of a low oil absorption silica abrasive useful in the practice of the present invention. The abrasive is present in the oral care composition of the present invention at a concentration of about 10 to about 60% by weight, in other embodiment about 20 to about 45% by weight, and in another embodiment about 30 to about 50% by weight.

The oral care compositions of the invention also may include an agent to increase the amount of foam that is produced when the oral cavity is brushed.

Illustrative examples of agents that increase the amount of foam include, but are not limited to polyoxyethylene and certain polymers including, but not limited to, alginate polymers.

The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide.

The polyoxyethylene may be present in an amount of about 1% to about 90%, in one embodiment about 5% to about 50% and in another embodiment about 10% to about 20% by weight of the oral care carrier component of the oral care compositions of the present invention. The dosage of foaming agent in the oral care composition (i.e., a single dose) is about 0.01 to about 0.9% by weight, about 0.05 to about 0.5% by weight, and in another embodiment about 0.1 to about 0.2% by weight.

The compositions useful in the invention may contain anionic surfactants. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. For example, concentrations used or a mouthwash are typically on the order of one tenth that used for a toothpaste. In one embodiment, the anionic surfactant is present in a toothpaste at from about 0.3% to about 4.5% by weight, e.g., about 1.5%.

The compositions of the invention may optionally contain mixtures of surfactants, comprising anionic surfactants and other surfactants which may be anionic, cationic, zwitterionic or nonionic. Generally, surfactants are those which are reasonably stable throughout a wide pH range. Surfactants are described more fully, for example, in U.S. Pat. No. 3,959,458, to Agricola et al.; U.S. Pat. No. 3,937,807, to Haefele; and U.S. Pat. No. 4,051,234, to Gieske et al., which are incorporated herein by reference.

In a particular embodiment, the composition comprises sodium lauryl sulfate.

The surfactant or mixtures of compatible surfactants can be present in the compositions of the present invention in about 0.1% to about 5.0%, in another embodiment about 0.3% to about 3.0% and in another embodiment about 0.5% to about 2.0% by weight of the total composition.

The oral care compositions of the invention may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint.

The flavoring agent may be incorporated in the oral composition at a concentration of about 0.1 to about 5% by weight and about 0.5 to about 1.5% by weight. The dosage of flavoring agent in the individual oral care composition dosage (i.e., a single dose) is about 0.001 to 0.05% by weight and in another embodiment about 0.005 to about 0.015% by weight.

Sweetening agents which can be used include sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, in particular sucralose, sodium cyclamate and sodium saccharin, and mixtures thereof. A composition preferably contains from about 0.1% to about 10% of these agents, preferably from about 0.1% to about 1%, by weight of the total composition.

The oral care compositions of the invention also may optionally include one or more chelating agents able to complex calcium found in the cell walls of the bacteria. Binding of this calcium weakens the bacterial cell wall and augments bacterial lysis.

Another group of agents suitable for use as chelating agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least about 1.0 wt. % pyrophosphate ions, about 1.5 wt. % to about 6 wt. %, about 3.5 wt. % to about 6 wt. % of such ions.

Gelled mineral oils are suitable hydrophobic viscosity modifiers. In some embodiments, the gelled mineral oil is preferably a blend of mineral oil and polyethylene, e.g. PLASTIGEL 5, which is a blend of 5% polyethylene in mineral oil, and is available from Pharmaceutical Resources/Lyne Laboratories Inc. of Brockton, Mass. Other suitable plastigels can be prepared in accordance with the teachings of Thau et al., "A New Procedure for the Preparation of Polyethylene-Mineral Oil Gels," J. Soc. Cosmetic Chemists, 16, 359-363 (1965). Suitable hydrophobic viscosity modifiers additional to gelled mineral oils, such as plastigels, can be identified by using the present disclosure as a guide.

The oral care compositions of the invention also optionally include one or more polymers. Polymers can provide certain advantages to the composition, for example when the composition is in the form of a toothpaste or gel, during preparation it is frequently necessary to add some thickening material to provide a desirable consistency of the composition, to provide desirable active release characteristics upon use, to provide shelf stability, and to provide stability of the composition, etc. Typical examples of polymers that can be present in the composition of the invention include polyethylene glycols, polyvinylmethyl ether maleic acid copolymers, polysaccharides (e.g., cellulose derivatives, for example carboxymethyl cellulose, or polysaccharide gums, for example gum karaya, gum arabic, gum tragacanth, xanthan gum or carrageenan gum). Acidic polymers, for example polyacrylate gels, may be provided in the form of their free acids or partially or fully neutralized water soluble alkali metal (e.g., potassium and sodium) or ammonium salts.

Particularly when noncationic antibacterial agents or antibacterial agents, e.g., triclosan, are included in any of the dentifrice components, there is also preferably included from about 0.05 to about 5% of an agent which enhances the delivery and retention of the agents to, and retention thereof on oral surfaces. Such agents useful in the present invention are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 30,000 to about 800,000. These copolymers are available for example as Gantrez. e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging from about 0.05 to about 3% by weight.

A particular class of thickening or gelling agents includes a class of homopolymers of acrylic acid crosslinked with an alkyl ether of pentaerythritol or an alkyl ether of sucrose, or carbomers. Orally acceptable carbomers are commercially available from B. F. Goodrich.

In certain embodiments, thickening agents in an amount of about 0.1% to about 15.0% by weight of the total composition are used, in another embodiment from about 0.5% to about 8%, in another embodiment from about 0.5% to about 5%.

Within certain embodiments of the oral compositions, it is also desirable to incorporate a humectant to prevent the composition from hardening upon exposure to air. Certain humectants can also impart desirable sweetness or flavor to dentifrice compositions. The humectant, on a pure humectant basis, generally includes about 15% to about 70% in one embodiment or about 30% to about 65% in another embodiment by weight of the dentifrice composition.

Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the toothpaste compositions herein.

In addition to the above described components, the embodiments of this invention can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

The compositions of the present invention can be made using methods which are common in the oral product area.

As used throughout, ranges are used as shorthand for describing each and every value that is within the range. Any value within the range can be selected as the terminus of the range. In addition, all references cited herein are hereby incorporated by reference in their entireties.

In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention as many variations are possible without departing from the spirit and scope thereof.

Various modifications of the invention in addition to those shown and described herein should be apparent to those skilled in the art and are intended to fall within the appended claims.

EXAMPLES

Example 1

ZG was prepared following a procedure outlined in U.S. Pat. No. 7,897,799 and Pappas I., et al., *Crystal Growth & Design*, 2009 (9):5213-5219. 20 µL of ZG was dissolved in 1 mL of deionized water to prepare a 2% ZG solution for simple experiments. To determine if ZG could precipitate from solution upon contact with saliva, 0.3 mL of the 2% ZG solution was added to 0.3 mL of clarified saliva. A large amount of precipitation was observed and it did not dissipate even after 24 hrs. The pH of the 1:1 saliva: 2% ZG system was 7.1. This experiment demonstrates that ZG will precipitate upon contact with components of human saliva.

Example 2

To determine if the ZG precipitate would occlude dentin tubules, a dentin disk is prepared. The disk is obtained from an extracted human molar. The disk is etched for 40 sec in 6% citric acid and sonicated for 30 min in deionized water to open up the dentin tubules. Each blank disk is imaged on the confocal microscope and the average area covered per tubule in a 100×125 µm region is calculated using image analysis software. Each disk is soaked in clarified human saliva overnight. The disk is removed from the saliva and 40 µL of 2% ZG solution is placed on the disk. After two minutes, the disk is rinsed with deionized water. The disk is imaged with the confocal microscope and the average % area covered per tubule in a 100×125 µm region is calculated using image analysis software. The % reduction in the area covered before and after treatment is reported in Table 1. The change in mean tubule diameter is also reported.

TABLE 1

|  | % Reduction in tubule area | % reduction in mean tubule diameter |
|---|---|---|
| 2% ZG on saliva coated dentin | 64 | 56 |

The data described in Table 1 (above) demonstrates that ZG can precipitate upon reaction with saliva, in an amount sufficient to occlude dentin tubules.

Example 3

2% ZG is incorporated in two carriers: a first comprising glycerin; and a second comprising the hydrophobic carrier MCT (medium chain triglycerides). The ability of each of these compositions to occlude dentin tubules is measured using hydraulic conductance.

Dentin disks are prepared and tubules opened, as described above. Each disk is soaked in PBS (phosphate buffer solution), which contains the salts present in saliva. The flow rate of water through each PBS soaked disk is measured before treatment. 65 µL of a 2% ZG solution is added to the disk. After 2 min, the ZG solution is removed and the disk is rinsed 5 times with 400 µL PBS. The flow rate of water through the dentin tubules after one treatment is measured. The percentage (%) reduction in fluid flow versus baseline is reported in Table 2 (below).

TABLE 2

| Segment | Treatment | % Reduction in Fluid Flow | Avg. % Reduction in Fluid Flow |
|---|---|---|---|
| A | 2% ZG in Glycerin | 39 | 25 |
| B | 2% ZG in Glycerin | 21 |  |
| E | 2% ZG in Glycerin | 22 |  |
| F | 2% ZG in Glycerin | 16 |  |
| I | 2% ZG in MCT | 71 | 79 |
| J | 2% ZG in MCT | 87 |  |

The data described in Table 2 (above) demonstrates that the compositions of the present invention provide a significantly greater reduction in fluid flow through the dentine tubules compared to similarly formulated compositions which do not contain the inventive combinations discovered by the present inventors.

The invention claimed is:

1. A substantially anhydrous oral composition comprising an effective amount of a zirconium amino acid complex suspended in a hydrophobic carrier for preventing, reducing or inhibiting dentinal hypersensitivity.

2. The composition of claim 1 wherein the zirconium amino acid complex is selected from a zirconium glycine complex, a zirconium alanine complex, a zirconium arginine complex, a zirconium threonine complex, a zirconium lysine complex, a zirconium leucine complex, a zirconium tryptophan complex, a zirconium phenylalanine complex, a zirconium valine complex, a zirconium methionine complex, and a combination of two or more thereof.

3. The composition of claim 1, wherein the zirconium amino acid complex is a zirconium glycine complex.

4. The composition of claim 1, wherein the hydrophobic carrier comprises an ingredient selected from: an oil; a wax; silicone; and a combination of two or more thereof.

5. The composition of claim 1, wherein the hydrophobic carrier comprises an oil selected from: a vegetable oil; a silicone oil; and a combination thereof.

6. The composition of claim 1, wherein the hydrophobic carrier comprises a C6 to C12 triglyceride.

7. The composition of claim 1, wherein the hydrophobic carrier comprises medium chain triglycerides (MCT), polyethylene glycol, silicone fluid, mineral oil, propylene glycol or a combination of two or more thereof.

8. The composition of claim 1 wherein the hydrophobic carrier comprises MCT.

9. The composition of claim 1 wherein the zirconium amino acid complex is present in the amount of about 0.01 wt. % to about 20 wt. % of the total composition weight.

10. The composition of claim 1, further comprising an abrasive.

11. The composition of claim 1, wherein the composition is a mouthrinse or a toothpaste.

12. A method of preventing, reducing or inhibiting dentinal hypersensitivity comprising applying an effective amount of the composition of any foregoing claim to the oral cavity of a subject in need thereof.

13. A method of occluding dentin tubules, comprising administering the composition of claim 1 to a subject in need thereof.

* * * * *